(12) United States Patent
McKinley et al.

(10) Patent No.: US 11,529,205 B2
(45) Date of Patent: Dec. 20, 2022

(54) PRECISION INJECTOR/EXTRACTOR FOR ROBOT-ASSISTED MINIMALLY-INVASIVE SURGERY

(71) Applicant: The Regents of the University of California, Oakland, CA (US)

(72) Inventors: Stephen McKinley, Berkeley, CA (US); Animesh Garg, Berkeley, CA (US); Sachin Patil, Burlingame, CA (US); Susan M. L. Lim, Singapore (SG); Ken Goldberg, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 709 days.

(21) Appl. No.: 15/738,482

(22) PCT Filed: Jun. 23, 2016

(86) PCT No.: PCT/US2016/039026
§ 371 (c)(1),
(2) Date: Dec. 20, 2017

(87) PCT Pub. No.: WO2016/210135
PCT Pub. Date: Dec. 29, 2016

(65) Prior Publication Data
US 2018/0177558 A1 Jun. 28, 2018

Related U.S. Application Data

(60) Provisional application No. 62/183,638, filed on Jun. 23, 2015.

(51) Int. Cl.
*A61B 34/35* (2016.01)
*A61M 5/20* (2006.01)
(Continued)

(52) U.S. Cl.
CPC .......... *A61B 34/35* (2016.02); *A61B 10/0233* (2013.01); *A61B 34/00* (2016.02);
(Continued)

(58) Field of Classification Search
CPC ..... A61B 10/0233; A61B 34/35; A61B 34/32; A61B 34/77; A61B 2017/0042;
(Continued)

(56) References Cited

U.S. PATENT DOCUMENTS 5,527,339 A * 6/1996 Koscher ................ A61B 17/29
606/205
5,893,875 A * 4/1999 O'Connor ............. A61B 17/29
606/174

(Continued)

OTHER PUBLICATIONS

International Search Report and Written Opinion in International Patent Application No. PCT/US2016/039026, dated Sep. 12, 2016.

*Primary Examiner* — Theodore J Stigell
(74) *Attorney, Agent, or Firm* — Venable LLP; Henry J. Daley; Aziz H. Poonawalla

(57) ABSTRACT

According to some embodiments of the invention, a surgical robot includes a robot arm having an end effector, the end effector comprising a needle assembly. The surgical robot further includes a robot control system operatively connected to the robot arm, and an end effector control system operatively connected to the end effector. The robot control system provides control signals for operation of the robot arm to move the end effector to selected positions relative to a subject. The end effector control system is configured to provide signals for operation of the end effector to at least one of inject material through the needle assembly to a selected location within the subject's body or extract material through the needle assembly from the selected location within the subject's body.

11 Claims, 9 Drawing Sheets

(51) Int. Cl.
*A61B 34/32* (2016.01)
*A61B 34/00* (2016.01)
*A61B 90/00* (2016.01)
*A61B 34/30* (2016.01)
*A61B 10/02* (2006.01)
*B25J 9/16* (2006.01)
*A61B 17/3211* (2006.01)

(52) U.S. Cl.
CPC ............ *A61B 34/30* (2016.02); *A61B 34/32* (2016.02); *A61B 34/77* (2016.02); *A61B 90/00* (2016.02); *A61M 5/20* (2013.01); *B25J 9/1697* (2013.01); *A61B 17/3211* (2013.01); *A61B 90/361* (2016.02); *A61B 2010/0208* (2013.01); *A61M 2205/50* (2013.01); *Y10S 901/02* (2013.01); *Y10S 901/41* (2013.01); *Y10S 901/47* (2013.01)

(58) Field of Classification Search
CPC ........... A61B 2017/00464; A61B 2017/00486; A61B 2017/00477; A61B 2017/0046; A61B 2017/00473; A61B 2017/2931; A61B 34/30; A61B 34/00; A61B 90/00; A61B 17/3211; A61B 2010/0208; A61M 5/20
See application file for complete search history.

(56) References Cited

U.S. PATENT DOCUMENTS

| | | | |
|---|---|---|---|
| 6,245,028 B1 | 6/2001 | Furst et al. | |
| 6,309,397 B1* | 10/2001 | Julian | A61B 34/30 128/898 |
| 7,367,973 B2* | 5/2008 | Manzo | A61B 34/37 606/49 |
| 7,922,688 B2* | 4/2011 | Bodduluri | A61B 17/3468 604/62 |
| 7,960,935 B2 | 6/2011 | Farritor et al. | |
| 2006/0079889 A1* | 4/2006 | Scott | A61B 18/1445 606/45 |
| 2008/0039255 A1* | 2/2008 | Jinno | A61B 17/29 474/148 |
| 2010/0094312 A1* | 4/2010 | Ruiz Morales | A61B 34/35 606/130 |
| 2010/0274202 A1 | 10/2010 | Hyde et al. | |
| 2012/0190981 A1 | 7/2012 | Harris et al. | |
| 2013/0172859 A1* | 7/2013 | Kaercher | A61B 17/2909 606/1 |
| 2013/0184690 A1* | 7/2013 | Doyle | A61B 34/70 606/1 |
| 2016/0067868 A1* | 3/2016 | Porter | B25J 15/04 74/490.06 |
| 2017/0056038 A1* | 3/2017 | Hess | A61B 17/29 |
| 2020/0155244 A1* | 5/2020 | Sevimli | A61B 34/30 |

* cited by examiner

PRECISION INJECTOR/EXTRACTOR FOR ROBOT-ASSISTED MINIMALLY-INVASIVE SURGERY

This application is a U.S. National Stage Application under 35 U.S.C. § 371 of PCT/US2016/039026, filed on Jun. 23, 2016, and claims the benefit of U.S. Provisional Application No. 62/183,638 filed Jun. 23, 2015, the entire contents of which are hereby incorporated by reference.

This invention was made with U.S. Government support under grant number IIS-1227536 awarded by the National Science Foundation. The U.S. Government has certain rights in the invention.

BACKGROUND

Technical Field

The field of the currently claimed embodiments of this invention relates to fluid injectors, and more particularly to equipping minimally-invasive robotic surgical-assist systems with fluid injectors.

2. Motivation for Fluidic Injection

Recent advances in stem-cell based tissue engineering research hold promise for near-term clinical application as regenerative therapies and for the treatment of a diverse set of debilitating conditions including liver disease and connective tissue disease [4]. Mesenchymal stem cells (MSCs) are cellular progenitors found to reside within bone marrow [5]. MSCs have shown pluripotency to replicate and differentiate into most somatic cellular types [6]. Transplants of a patient's own undifferentiated mesenchymal stem cells to areas outside of the bone marrow can prompt MSC specialization to that of their residing location providing repair or regeneration of that tissue [7].

While there is extensive research on methodologies to harness and differentiate stem cells, there is less innovation and no clear consensus on viable modes of stem cell delivery in the clinic [8]. Systemic delivery employs an intravenous injection of high volumes of cells with the expectation that some of the injected cells will migrate to the targets of interest [9]. However, systemic delivery of stem cells in very high numbers also introduces risk for pulmonary emboli or infarction, as many of the cells will become trapped in the lung [10]. Local delivery via direct injections allow for controlled and precise stem cell delivery to organs in more inaccessible locations within the thorax, abdomen and pelvis, but is challenging because of its relatively high degree of invasiveness [10]. Novel procedures or delivery devices are needed to reach certain anatomic locations such as organs located within the abdominal cavity [8].

Minimally-invasive robotic surgical-assist systems are designed to aid surgeons in performing high-precision tasks. In a tele-operative minimally-invasive robotic surgical-assist system, a surgeon sits in a console that is remote from the surgical cite, and uses instruments such as joysticks to control a robot that is located at the surgical cite. The robot has at least one arm that includes a tool holder, to which a surgical tool is attached. The surgeon moves the joysticks to control the position of the surgical tool. For tasks requiring a high degree of precision, the system can be configured to scale the surgeon's motions such that the movement of the surgical tool is small compared to the force exerted by the surgeon on the joystick.

The console in which the surgeon sits includes a display that allows the surgeon to view the surgical site and the operating tools. Thus, a minimally-invasive robotic surgical-assist system enables a surgeon to view the surgical site and move a surgical tool to a precise location for interacting with a patient's tissue. Such systems often employ a grasping tool such as forceps that can be actuated remotely by the surgeon to grasp or release tissue or other objects.

During many surgical procedures, the surgeon is required to dispense a material in a precise location. For example, the surgeon could be required to apply a surgical adhesive to close a wound, or to dispense a material in a precise location to act as a fiducial marker for imaging or operating. The surgeon could be required to inject or dispense T-cells, collagen gel, or fluids or fluid media containing stem cells or drug-eluting chemotherapy beads, for example. The material could be a fluid or powder or could comprise smaller solid objects such as radio-active seeds, for example. While the surgeon could benefit from the high-precision positioning capabilities of a minimally-invasive robotic surgical-assist system, current robotic surgical-assist systems do not include a delivery device or method for injecting a material. The systems include neither the hardware nor the software for performing an injection using a minimally-invasive robotic surgical-assist system.

In addition to injecting or depositing material, many surgical procedures require the surgeon to take a biopsy. To take the biopsy, the surgeon may introduce a needle or other instrument into the tissue to collect a sample of the tissue. The positioning of the biopsy tool may require a high degree of precision, such as that afforded by a minimally-invasive robotic surgical-assist system. However, current robotic surgical-assist systems do not include a needle or other tool that can be used to collect biopsy samples.

Discussion of Related Art

One example of a minimally-invasive robotic surgical-assist system is the Intuitive Surgical da Vinci robot. Da Vinci robots were used to perform 570,000 surgeries in 2014 using more than 3,000 individual devices (with over 2,000 in the United States) [11]. A number of other companies make related minimally-invasive robotic surgical-assist systems. However, as described above, these systems are not equipped with hardware or software that allows them to be used for injecting or extracting material. Accordingly, there remains a need for improved devices and methods for use with minimally-invasive robotic surgical-assist systems.

SUMMARY

According to some embodiments of the invention, a surgical robot includes a robot arm having an end effector, the end effector comprising a needle assembly. The surgical robot further includes a robot control system operatively connected to the robot arm, and an end effector control system operatively connected to the end effector. The robot control system provides control signals for operation of the robot arm to move the end effector to selected positions relative to a subject. The end effector control system is configured to provide signals for operation of the end effector to at least one of inject material through the needle assembly to a selected location within the subject's body or extract material through the needle assembly from the selected location within the subject's body.

According to some embodiments of the invention, an end effector assembly for use with a surgical robot includes a needle assembly having an adapter section configured to connect to an end effector of a surgical robot arm, and a needle control system operatively connected to the needle assembly. The needle control system is configured to provide signals for operation of the needle assembly to at least one of inject material through the needle assembly to a selected location within a subject's body or extract material through the needle assembly from the selected location within the subject's body.

BRIEF DESCRIPTION OF THE DRAWINGS

Further objectives and advantages will become apparent from a consideration of the description, drawings, and examples.

DETAILED DESCRIPTION

Figure 1:
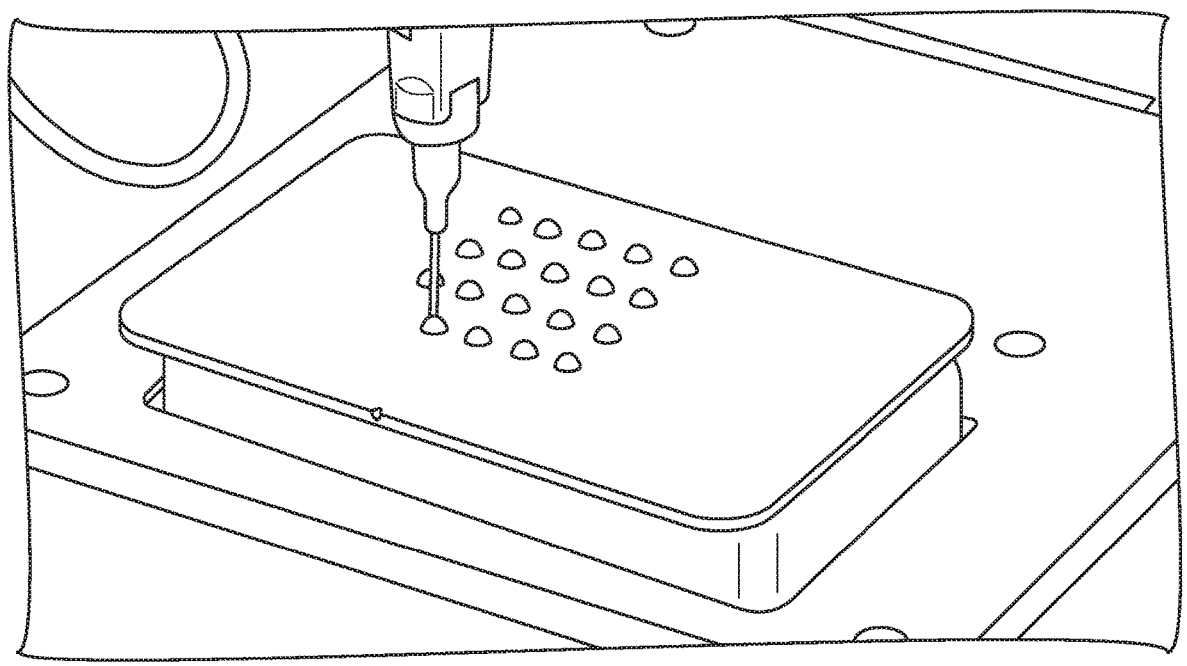
FIG. 1 illustrates precisely spaced injections by a surgical robot according to some embodiments of the invention around a target area.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Accordingly, an embodiment of the current invention provides a surgical robot and an end effector assembly for use with a surgical robot that can facilitate minimally invasive infusion of material, such as, but not limited to, stem cells, time-release chemotherapy beads, surgical glue, or other materials where indicated, at any location already accessible by a surgical robot, such as, but not limited to the surgical robot [1-3]. The surgical robot and end effector assembly, according to an embodiment of the current invention, enable delivery of measured amounts of a material to a desired site within the body using minimally invasive surgical instruments. The surgical robot and end effector assembly can also be used to extract material from a precise location, for example, to collect a biopsy. According to some embodiments, the end effector of the surgical robot has a needle assembly for injecting material through said needle assembly to a selected location within a patient's body, or extract material through said needle assembly from a selected location within said subject's body. According to some embodiments, an end effector assembly is coupled with a surgical robot. A software interface between the control system of the conventional surgical robot and the control system of the needle assembly is described. The needle assembly for the conventional surgical robot allows for injection and/or extraction of material into or from a precise location without increasing the overall size of the conventional surgical robot's end effector.

The surgical robot and end effector assembly for use with a surgical robot described herein can have a variety of applications. For example, many treatment processes require material to be injected or deposited in a precise location. A surgical robot can enhance a surgeon's ability to accurately deliver the treatment by allowing the surgeon to better visualize the treatment cite, and to precisely move the end effector to the exact location for treatment. A surgical procedure may also require a surgeon to extract material from a precise location. A surgical robot can enable the surgeon to position the extraction tool, for example, a needle, to a precise location, and can allow the surgeon to view the surgical cite as the material is extracted. The surgical robot system may display preoperative data that the surgeon can consult during the injection procedure. The surgical robot system may also have image capture and display systems that provide real-time images of the surgical site for the surgeon to view while performing the procedure. Real-time and pre-operative data could be registered or combined in such a way as to improve accuracy and precision of the material injections and/or extractions.

The term "material" as used herein is intended to have a broad meaning. It can include anything that may be injected to, or extracted from, a subject through a needle. It can include, but is not limited to, fluids, liquids, suspensions in which particles are suspended in a liquid, emulsions, gels, powders, tissue, biological cells and any combinations thereof.

The term "fluid" is used herein to indicate a material that can be injected or extracted using a needle assembly. The fluid may be a liquid or a gas, and/or may include solid particles. For example, the fluid may be a powder. The fluid may be homogenous, or may comprise materials having different properties, such as seeds or beads suspended in a liquid. Example fluids include, but are not limited to, tissue, T-cells, anesthesia, collagen gel, or fluids or fluid media containing stem cells or drug-eluting chemotherapy beads.

The term "subject" is intended to include humans and animals, for example.

In some cases, a treatment may require a surgeon to deposit a material in a particular pattern. One example is delivering stem cells to a particular organ or tissue region in a precise grid pattern with precise quantities injected at each grid location. Another example is depositing radioactive seeds at precise grid locations within a three-dimensional grid pattern for use during radiation therapy, for example. Another example is distributing anesthesia such that it uniformly covers a region of interest. These are only a couple of possible applications. The general concepts of the current invention are not limited to these examples. FIG. 1 shows an example of precise deposition of a fluid using an end effector assembly according to some embodiments of the current invention. The surgeon can control the robot arm and end effector assembly to inject the material in the desired locations. Alternatively, the surgeon may identify the location or locations for treatment, for example, using an interactive display, and then the surgical robot may autonomously, or semi-autonomously, perform the deposition of the material using the end effector assembly. The robot may aid the surgeon in injecting or extracting material into or from tissue that is moving. For example, the robot may observe and respond to repetitive motion, such as the movement of a beating heart or breathing lungs, to precisely position the tool with respect to the tissue. This may require the robot to continuously compensate for the motion of the tissue during the injection or extraction process. The robot may also be configured to respond to non-repetitive or unexpected motion of the tissue by compensating for the motion in order to perform the injection or extraction.

Tele-operated robotic systems are described as examples in several places throughout this description of embodiments of the current invention. However, the broad concepts of the current invention are not limited to tele-operated robots. Some embodiments of the current inventing could include cooperative controlled robots, and or, completely automated preprogrammed robots, for example. A cooperatively controlled robot is a robot that performs functions in cooperation with a user. For example, a user could grab the end effector and/or a position on the robotic arm towards the end effector. The cooperative control robot sense forces and/or torques applied by the user to respond in a particular way so as to assist the user in successfully completing the task.

Figure 2:
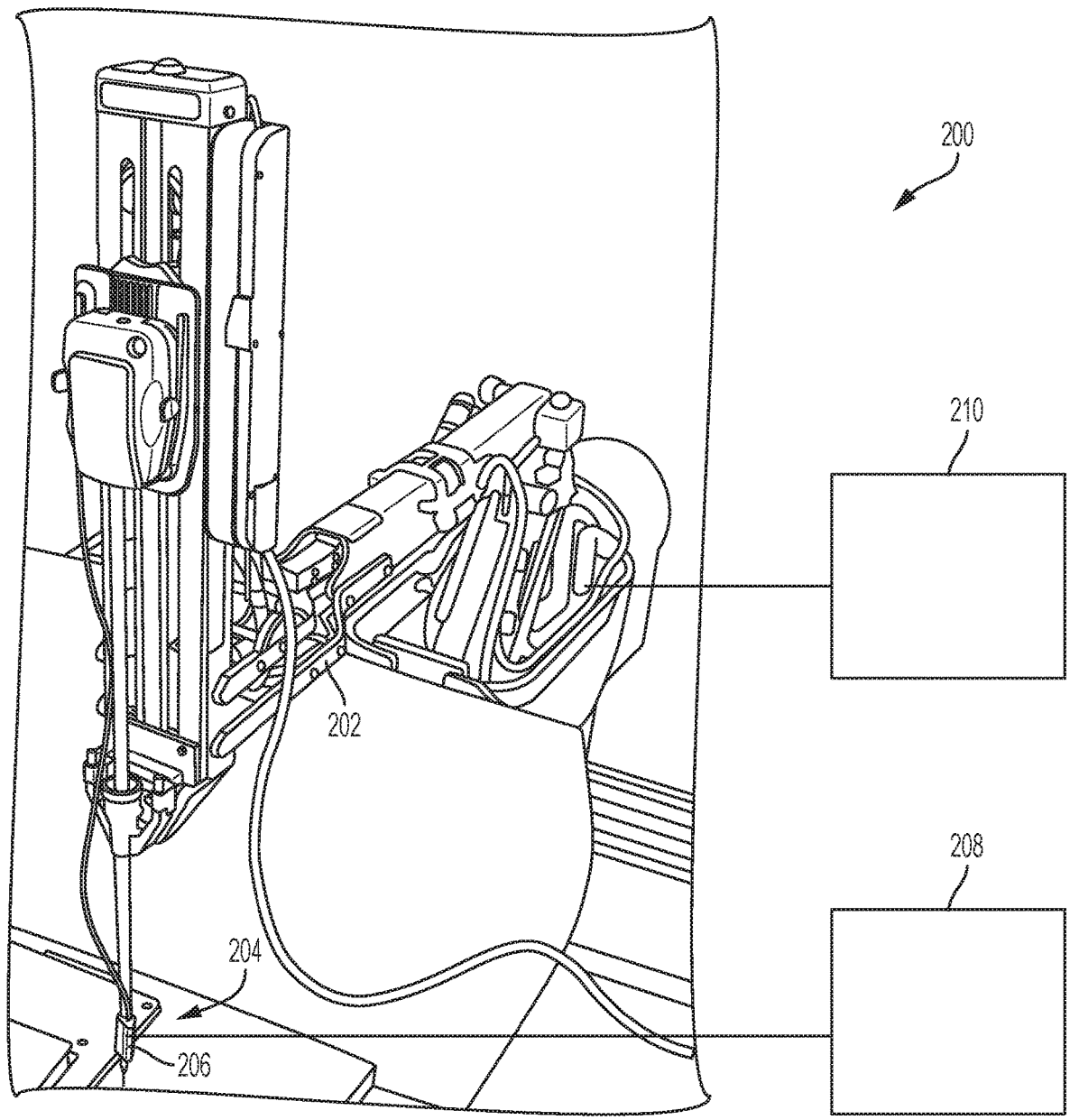
FIG. 2 shows a surgical robot according to some embodiments of the invention.

A surgical robot according to some embodiments of the invention is shown in FIG. 2. The surgical robot 200 includes a robot arm 202 having an end effector 204, the end effector 204 comprising a needle assembly 206. The surgical robot 200 also includes a robot control system 208 operatively connected to the robot arm 202, and an end effector control system 210 operatively connected to the end effector 204. The robot control system 208 provides control signals for operation of the robot arm 202 to move the end effector 204 to selected positions relative to a subject, and the end effector control system 210 is configured to provide signals for operation of the end effector 204 to at least one of inject material through the needle assembly 206 to a selected location within a subject's body or extract material through the needle assembly 206 from the selected location within the subject's body.

According to some embodiments, the needle assembly 206 comprises a needle defining a lumen therein that is suitable to allow the passage of the material through the lumen. The needle assembly 206 can further include a material compartment connected to the needle that is suitable to at least one of contain the material to be injected or contain the material to be extracted from the subject, and an actuator assembly that receives signals from the end effector control system to at least one of draw the material in from the subject through the lumen of the needle or force the material out through the lumen of the needle to be injected into the subject. According to some embodiments, the material compartment is configured to receive a syringe therein as is shown in an embodiment in FIG. 3.

Figure 3:
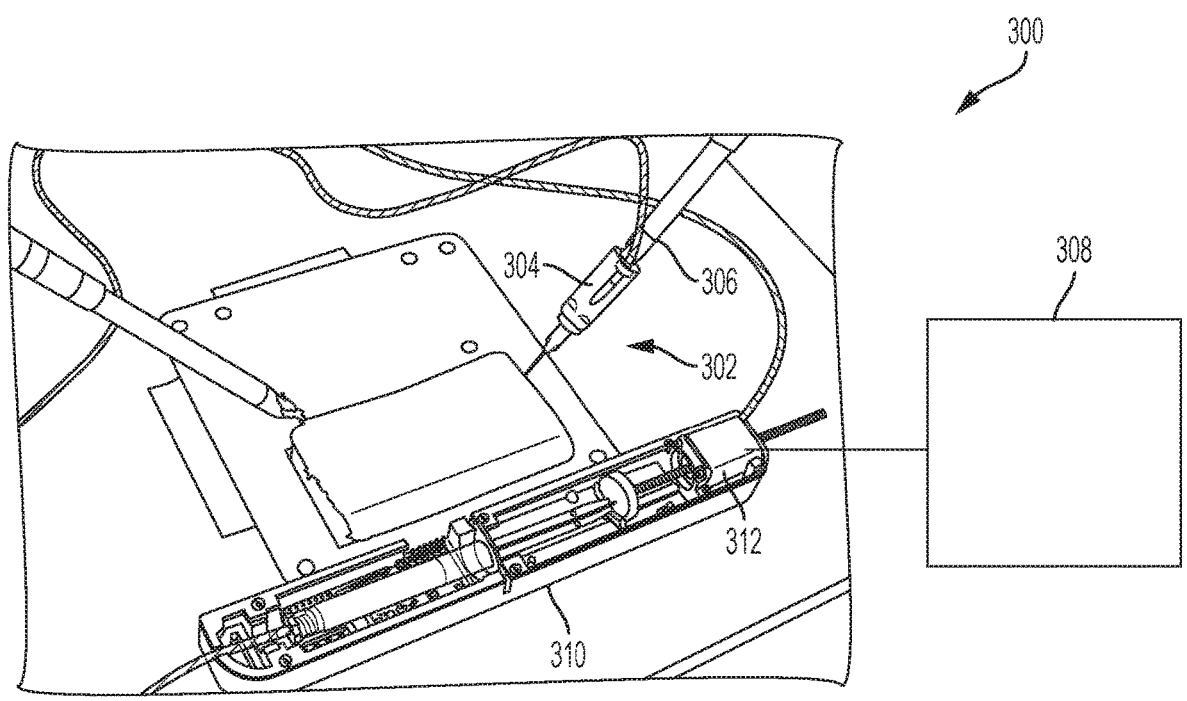
FIG. 3 is a schematic illustration of an end effector assembly according to some embodiments of the invention.

An end effector assembly 300 for use with a surgical robot according to some embodiments of the invention is shown in FIG. 3. The end effector assembly 300 includes a needle assembly 302 having an adapter section 304 configured to connect to an end effector 306 of a conventional robot arm. The end effector assembly 300 also includes a end effector control system 308 operatively connected to said needle assembly 302. The end effector control system 308 is configured to provide signals for operation of said needle assembly 302 to at least one of inject material through said needle assembly 302 to a selected location within a subject's body or extract material through said needle assembly 302 from said selected location within said subject's body.

According to some embodiments, the needle assembly 302 of the end effector assembly 300 comprises a needle defining a lumen therein that is suitable to allow the passage of the material through the lumen. The needle assembly 302 can further include a material compartment 310 connected to the needle that is suitable to at least one of contain the material to be injected or contain the material to be extracted from the subject. According to some embodiments, the material compartment is configured to receive a syringe therein, as shown in FIG. 3.

According to some embodiments, the needle assembly 302 further includes an actuator assembly 312 that receives signals from the end effector control system 308 to at least one of draw the material in from the subject through the lumen of the needle or force the material out through the lumen of the needle to be injected into the subject. The actuator assembly 312 can include a microcontroller in communication with said end effector control system 308. The microcontroller is configured to control motion of said actuator assembly 312 for at least one of drawing said material in from said subject through said lumen of said needle or forcing said material out through said lumen of said needle to be injected into said subject.

According to some embodiments of the invention, the actuator assembly 312 comprises a microcontroller configured to control the injection or extraction forces provided by the actuator assembly 312. The actuator assembly 312 can further include a stepper motor driver in communication with the microcontroller. The actuator assembly 312 can also include a linear actuator in communication with the stepper motor driver, wherein the linear actuator is configured to withdraw or advance in order to draw material in from the subject through the lumen of the needle or force said material out through the lumen of the needle to be injected into said subject.

Figure 4:
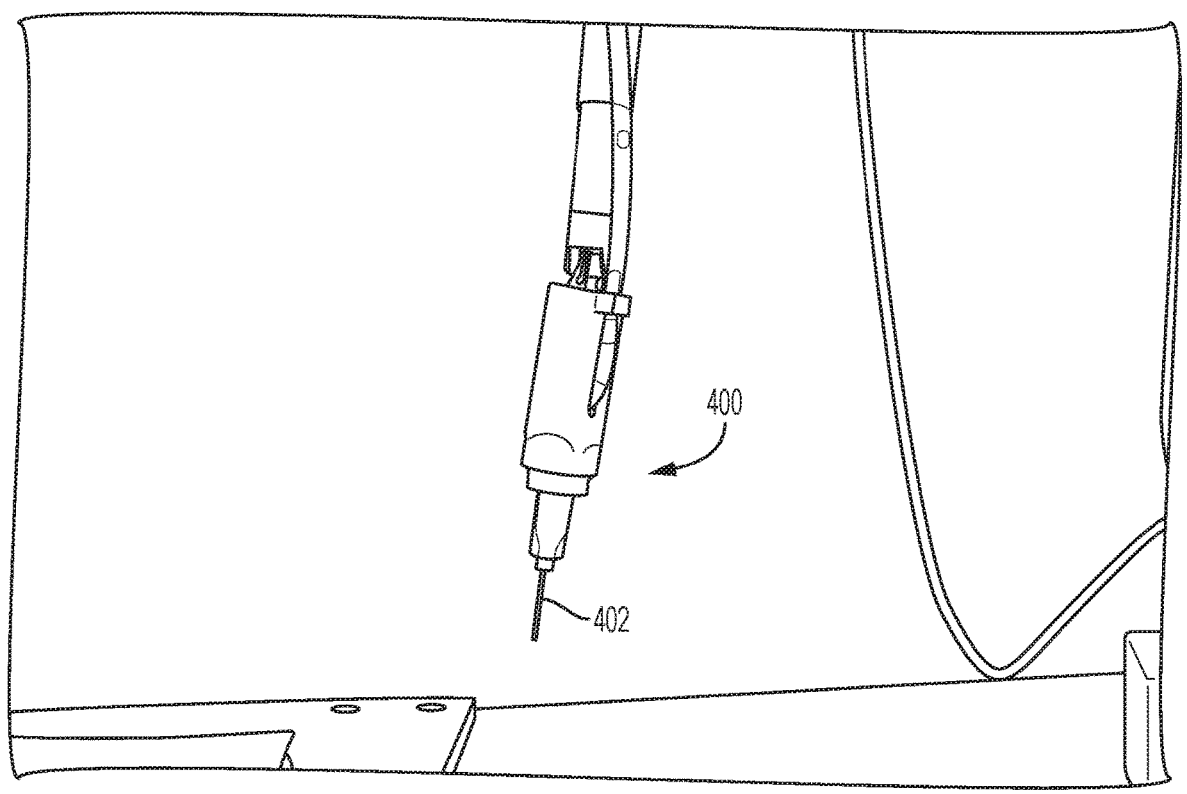
FIG. 4 shows an example injector in which the needle assembly includes a needle that is in fluid connection with a catheter.

FIG. 4 shows an example end effector assembly in which the needle assembly 400 includes a needle 402 that is in fluid connection with a catheter. According to some embodiments, the catheter is a flexible catheter that is in fluid connection with the material compartment.

Figure 5:
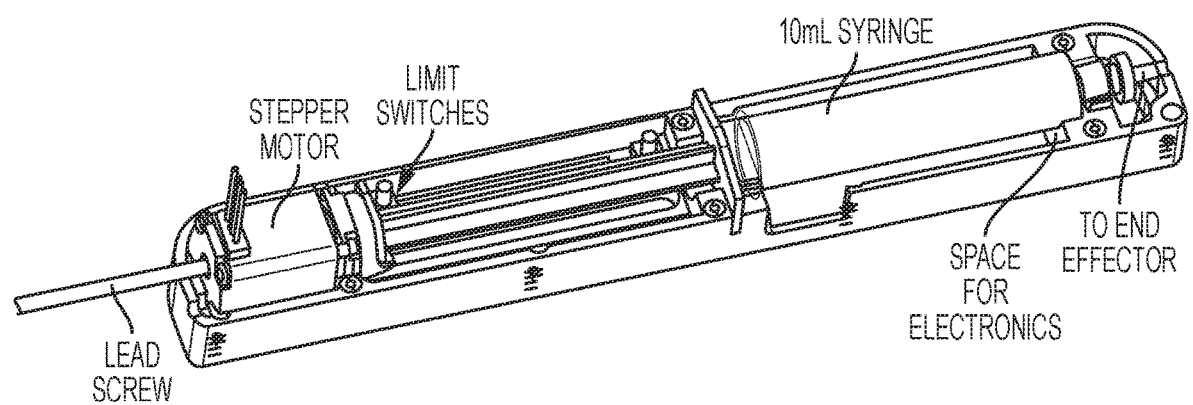
FIG. 5 shows an example of an actuator assembly having a stepper motor that can be actuated to compress a syringe.

FIG. 5 shows an example of an actuator assembly. As described above, the actuator assembly has a stepper motor that can be actuated to advance or withdraw, thereby injecting or extracting material through the needle.

Figure 6:
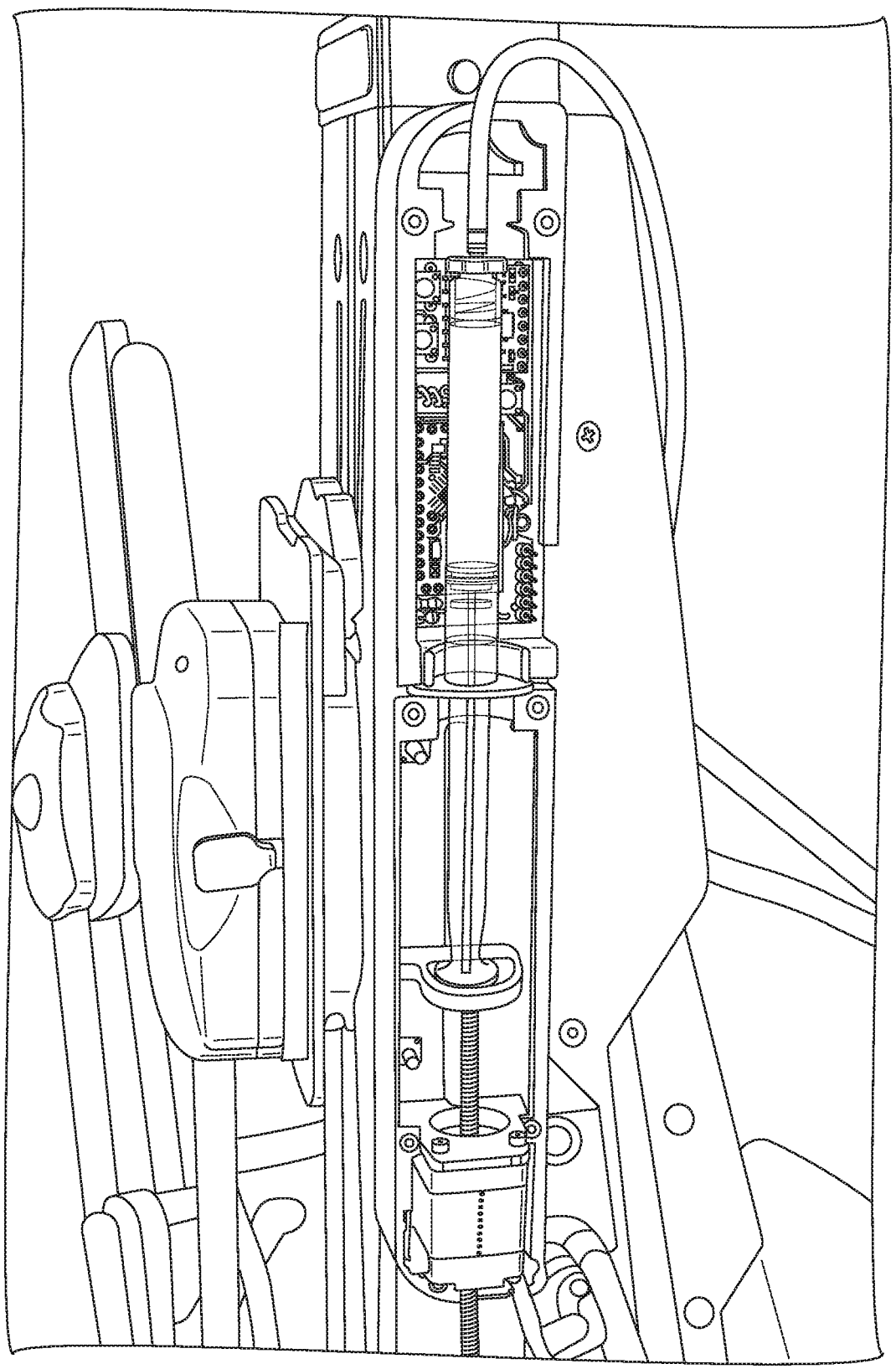
FIG. 6 shows an example of an injector assembly according to an embodiment of the current invention that is attached to an arm of a surgical robot.

According to some embodiments, a portion of the end effector assembly may be configured to attach to the robot arm. FIG. 6 shows an end effector assembly in which the material compartment and actuator assembly are attached to the robot arm. The robot arm may have preexisting screw holes into which the portion of the end effector assembly may be bolted. Other fastening mechanisms may also be used to attach a portion of the end effector assembly to the robot arm. The end effector assembly may include a casing with a cover for enclosing the material compartment and actuator assembly therein.

Figure 7:
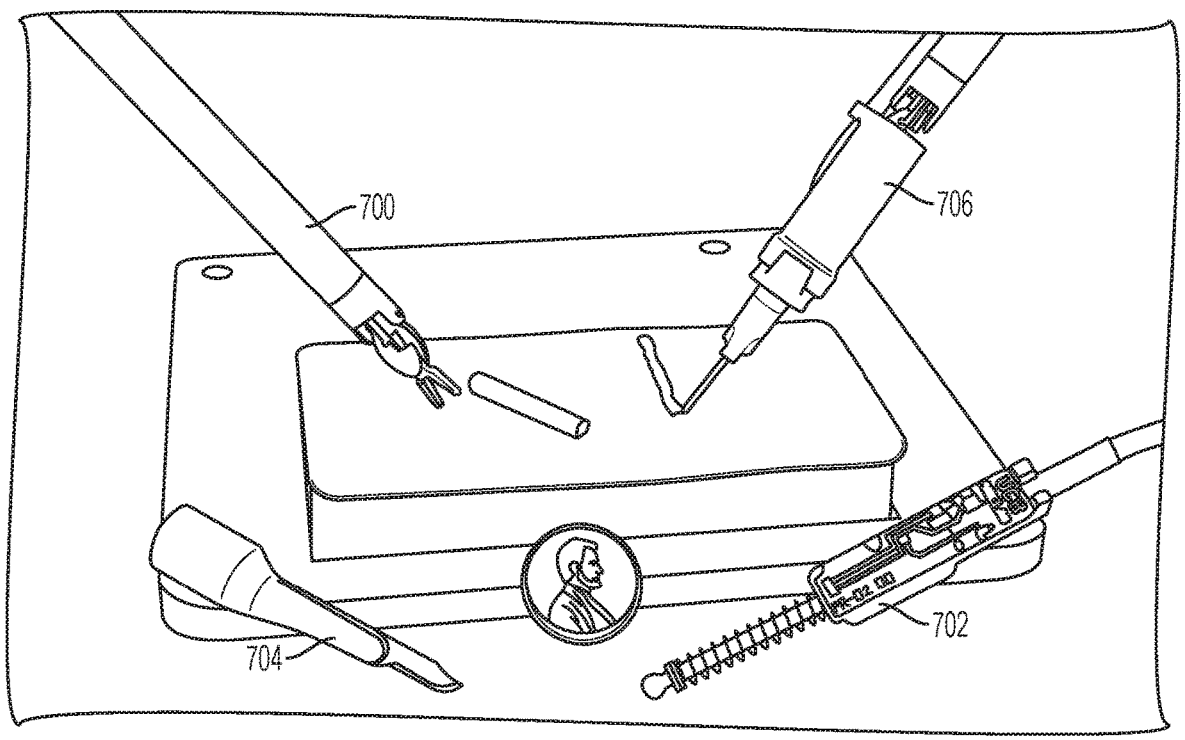
FIG. 7 shows an ecosystem of hardware designed to enable surgical automation of a surgical robot.
Figure 8:
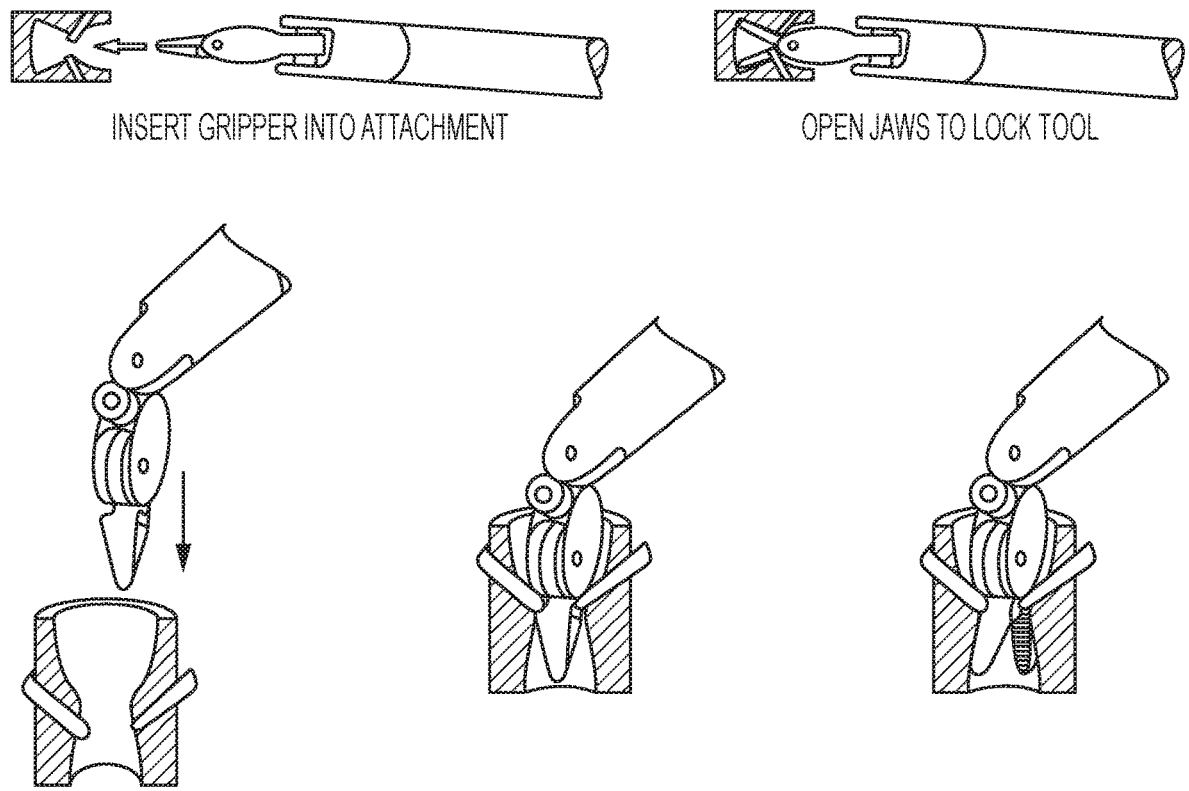
FIG. 8 shows an example in which a material compartment is included in the needle assembly.

According to some embodiments, the needle assembly is disposable. According to some embodiments, the needle assembly defines a cavity into which the end effector of the robot arm can be introduced. The cavity has a shape such that when the end effector is actuated within the cavity, the end effector engages the inner surface of the cavity such that the needle assembly is mechanically coupled to the end effector. For example, the end effector may be a controllable gripper, such as the gripper 700 in FIG. 7. FIG. 8 illustrates an example needle assembly and cavity, and a process for coupling the needle assembly to a gripper. The gripper, in its closed state, may be inserted into the needle assembly cavity.

The gripper may then be opened, engaging the inner surface of the cavity such that the needle assembly is mechanically coupled to the gripper. The embodiments of the invention are not limited to this coupling mechanism, and other methods for coupling the needle assembly to the end effector may be used. For example, the needle assembly could be held between the gripper jaws and secured by the gripper closing force rather than by gripper opening force.

The end effector assembly according to some embodiments comprises three components: a needle assembly, a flexible catheter assembly, and a drive motor assembly (also referred to as an "actuator assembly") mounted to a robot arm. In the case of a daVinci robot, for example, the actuator assembly can be mounted to the upper portion of the dVRK arm, behind the sterile barrier. An injection force can be provided by an actuator, such as a linear actuator. The linear actuator can be powered by a stepper motor driver, and controlled by a microcontroller. For example, the injection force can be provided by a Haydon-Kerk 21F4AC-2.5 linear actuator, powered by Allegro's A4988 microstepping bipolar stepper motor driver, and controlled by an Arduino Pro Mini 328 microcontroller. These components are purely exemplary, and the embodiments of the invention are not limited to these specific devices.

According to some embodiments of the invention, the end effector control system is integrated with the robot control system. This allows a surgeon to communicate with the end effector control system using the user interface provided by the surgical robot. A surgeon uses the robot control system to position the end effector, and then uses the robot control system to instruct the end effector control system to inject or extract material.

According to some embodiments of the invention, an additional control system communicates with both the robot control system and the end effector control system. A surgeon utilizes the additional control system to instruct the robot control system in the positioning of the robot end effector, and then uses the additional control system to instruct the end effector control system to inject or extract material.

According to some embodiments, the injector assembly can include a housing, as shown in FIG. 5. The housing can be 3D printed, for example. A disposable syringe is deposited in a cavity defined by the housing, and is moved along a linear stage. For example, the disposable syringe can be a 3 mL, 5 mL, or 10 mL syringe, though the embodiments of the invention are not limited to syringes having these volumes. The housing can be mounted to the robot arm.

According to some embodiments of the invention, the injector is created to fit within an ecosystem of hardware designed to enable surgical automation of a surgical robot, such as the dVRK Surgical Robot. FIG. 7 shows other devices including a palpation probe 702 and a scalpel 704 that may be used in addition to the gripper 700 and the end effector assembly 706. Each device has its own address on an i2c communication bus controlled by a master point that acts as a Robot Operating System (ROS) node. The end effector assembly can be commercialized as a standalone device or as an extension of currently available robotic surgical tools.

Figure 9:
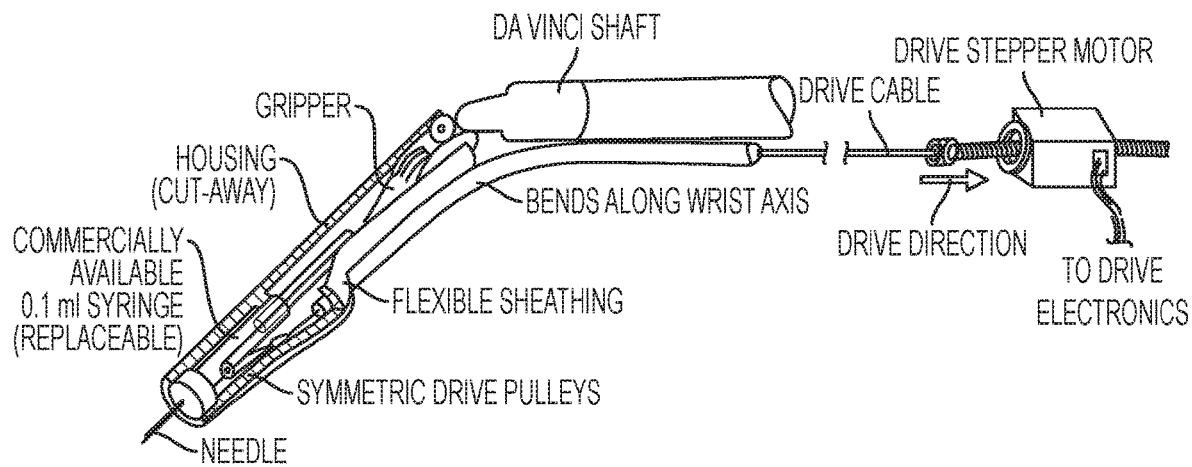
FIG. 9 shows another example of an injector assembly according to an embodiment of the current invention that is attached to an arm of a surgical robot.

According to some embodiments of the invention, the payload may be mounted at the end-effector rather than behind the sterile barrier. FIG. 9 shows an example in which a syringe is included in the needle assembly. The syringe can be actuated by an actuator assembly that can be removed from the region of interest. For example, the actuator assembly can be attached to the robot arm.

The following examples describe some embodiments in more detail. The broad concepts of the current invention are not intended to be limited to the particular examples. Further, concepts from each example are not limited to that example, but may be combined with other embodiments of the system.

Examples

Described herein is an instrument, shown in FIG. 2, mounted to a surgical robot that can deliver measured amounts of saline solution containing MSCs to desired sites within the body using Intuitive Surgical's da Vinci Robotic Surgical Assistant. A software interface between the existing da Vinci Research Kit (dVRK) and the injector hardware allows for treatment without increasing the overall size of the dVRK end-effector in-vivo. While some of the embodiments of the invention are described herein in conjunction with the da Vinci Robotic surgical system, the embodiments of the invention are not limited to use with a da Vinci Robotic surgical system. The system and methods can be adapted for any type of minimally invasive robot surgical system, including teleoperative, cooperative, and autonomous systems.

According to some embodiments of the invention, the injector comprises three components: a tool-tip mounted needle, a flexible catheter assembly, and a drive motor assembly mounted to the upper portion of the dVRK arm (behind the sterile barrier) as shown in FIG. 2. Typical local injection volume is on the order of 10's of milliliters, with per-injection doses of 10 mL to 30 mL representing approximately 10 million viable MSCs [12]. This volume guided the design of the injector to include an off-board dVRK syringe pump. Injection force is provided by a Haydon-Kerk 21F4AC-2.5 linear actuator, powered by Allegro's A4988 microstepping bipolar stepper motor driver, and controlled by an Arduino Pro Mini 328 microcontroller. A 10 mL syringe is carried by a 3D-printed enclosure along a linear stage that is mounted to the dVRK arm.

REFERENCES

[1] "Automated Delivery Instrument for Stem Cell Treatment using the da Vinci Robotic Surgical System." Stephen McKinley, Animesh Garg, Susan Lim, Sachin Patil, Ken Goldberg. 13th Annual Meeting of the International Society for Stem Cell Research. Stockholm, Sweden. June 2015.

[2] Stephen McKinley, Animesh Garg, Siddarth Sen, David V. Gealy, Jonathan P. McKinley, Yiming Jen, Menglong Guo, Doug Boyd, Ken Goldberg. "An Interchangeable Surgical Instrument System with Application to Supervised Automation of Multilateral Tumor Resection." IEEE International Conference on Automation Science and Engineering, (CASE), Dallas, Tex. August 2016. [.pdf] http://goldberg.berkeley.edu/pubs/case2016-interchangeable-instruments-submitted.pdf

[3] Stephen McKinley, Siddarth Sen, Animesh Garg, Yiming Jen, David Gealy, Pieter Abbeel, Ken Goldberg. "Robot-Assisted Surgery: Autonomous Tumor Localization and Extraction: Palpation, Incision, Debridement and Adhesive Closure with the da Vinci Research Kit" * Best Video Award * Hamlyn Surgical Robotics Conference, London, June 2015. (3 mins): https://youtu.be/YiPg9t0tR3U

[4] Wang, Shihua, Xuebin Qu, and Robert Chunhua Zhao. "Clinical applications of mesenchymal stem cells." J Hematol Oncol 5.1 (2012): 19.

[5] Friedenstein, Alexander Jakovlevich, et al. "HETEROTOPIC TRANSPLANTS OF BONE MARROW." Transplantation 6.2 (1968): 230-247.
[6] Phinney, Donald G., and Darwin J. Prockop. "Concise review: mesenchymal stem/multipotent stromal cells: the state of transdifferentiation and modes of tissue repair—current views." Stem cells 25.11 (2007): 2896-2902.
[7] Muschler, George F., Chizu Nakamoto, and Linda G. Griffith. "Engineering principles of clinical cell-based tissue engineering." The Journal of Bone & Joint Surgery 86.7 (2004): 1541-1558.
[8] Jung, Yunjoon, Gerhard Bauer, and Jan A. Nolta. "Concise review: induced pluripotent stem cell-derived mesenchymal stem cells: progress toward safe clinical products." Stem cells 30.1 (2012): 42-47.
[9] Devine, Steven M., et al. "Mesenchymal stem cells are capable of homing to the bone marrow of non-human primates following systemic infusion." Experimental hematology 29.2 (2001): 244-255.
[10] Karp, Jeffrey M., and Grace Sock Leng Teo. "Mesenchymal stem cell homing: the devil is in the details." Cell stem cell 4.3 (2009): 206-216.
[11] 'Intuitive Surgical Investor Presentation.' Available Online at http://investor.intuitivesurgical.com/phoenix.zhtml?c=122359&p=irol-IRHome.
[12] Tateishi-Yuyama, Eriko, et al. "Therapeutic angiogenesis for patients with limb ischemia by autologous transplantation of bone-marrow cells: a pilot study and a randomized controlled trial." The Lancet 360.9331 (2002): 427-435.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A robotic surgical system, comprising:
a robot arm having an end effector; and
a surgical device that is attachable and removable from said end effector;
wherein said end effector is a gripper that has an open state and a closed state, and
wherein said surgical device comprises an adapter configured to receive the gripper in the closed state and to couple to the gripper in the open state after receiving the gripper in the closed state.

2. The robotic surgical system of claim 1, wherein the surgical device is a needle assembly,
wherein said needle assembly comprises a needle defining a lumen therein that is suitable to allow passage of a material through said lumen during at least one of injection of said material to a selected location within a subject and extraction of said material from said selected location within said subject.

3. The robotic surgical system of claim 2, wherein said needle assembly further comprises:
a material compartment connected to said needle that is suitable to at least one of contain said material to be injected and contain said material to be extracted from said subject; and
an actuator assembly that is coupled to said material compartment to at least one of draw said material in from said subject through said lumen of said needle and force said material out through said lumen of said needle to be injected into said subject.

4. The robotic surgical system of claim 3, wherein said material compartment is configured to receive a syringe therein.

5. The robotic surgical system of claim 3, wherein said actuator assembly comprises a microcontroller that is configured to control motion of said actuator assembly for at least one of drawing said material in from said subject through said lumen of said needle and forcing said material out through said lumen of said needle to be injected into said subject.

6. The robotic surgical system according to claim 5, wherein the microcontroller is configured to communicate with the robot arm,
wherein said actuator assembly further comprises:
a stepper motor driver in communication with said microcontroller; and
a linear actuator operatively connected to said stepper motor driver, wherein the linear actuator is configured to withdraw and advance in order to draw said material in from the subject through the lumen of the needle and to force said material out through the lumen of the needle to be injected into said subject.

7. The robotic surgical system according to claim 2, wherein said robotic surgical system is configured for autonomous operation to move said gripper to a plurality of selected positions relative to said subject, and wherein said needle assembly is configured to at least one of inject said material through said lumen and extract said material through said lumen at each of said plurality of selected positions.

8. The robotic surgical system according to claim 1, wherein said robotic surgical system is a tele-operated robot.

9. The robotic surgical system according to claim 1, wherein said robotic surgical system is a cooperative-control robot.

10. The robotic surgical system according to claim 1, wherein said robotic surgical system is configured to move said gripper to selected positions relative to a subject while compensating for motion of said subject.

11. The robotic surgical system according to claim 1, wherein the surgical device is a needle assembly.

* * * * *